United States Patent
Nose et al.

(10) Patent No.: US 9,255,899 B2
(45) Date of Patent: Feb. 9, 2016

(54) NON-DESTRUCTIVE INSPECTION METHOD AND DEVICE

(75) Inventors: Hiroyuki Nose, Tokyo (JP); Hajime Kuwabara, Tokyo (JP); Tetsuya Kobayashi, Tokyo (JP)

(73) Assignee: IHI Corporation, Tokyo (JP)

( * ) Notice: Subject to any disclaimer, the term of this patent is extended or adjusted under 35 U.S.C. 154(b) by 475 days.

(21) Appl. No.: 13/501,468

(22) PCT Filed: Oct. 13, 2010

(86) PCT No.: PCT/JP2010/067973
§ 371 (c)(1),
(2), (4) Date: Apr. 12, 2012

(87) PCT Pub. No.: WO2011/046148
PCT Pub. Date: Apr. 21, 2011

(65) Prior Publication Data
US 2012/0199746 A1    Aug. 9, 2012

(30) Foreign Application Priority Data
Oct. 15, 2009    (JP) .................................. 2009-238317

(51) Int. Cl.
*G01N 23/22* (2006.01)
*G01N 23/222* (2006.01)

(52) U.S. Cl.
CPC .................................... *G01N 23/222* (2013.01)

(58) Field of Classification Search
CPC . G01N 23/22; G01N 23/2073; G01N 23/206; G01N 23/2206; G01N 23/2208; G01N 23/222
USPC ........ 250/269.2, 253, 265, 266, 269.4, 269.1, 250/269.6, 269.5, 361 R, 370.05, 390.01
See application file for complete search history.

(56) References Cited

U.S. PATENT DOCUMENTS 3,089,958 A * 5/1963 Janner ........................... 376/254
4,266,132 A * 5/1981 Marshall, III .............. 250/359.1
(Continued)

FOREIGN PATENT DOCUMENTS

| JP | 4 504310 | 7/1992 |
| JP | 7 301610 | 11/1995 |
| WO | 2008 012360 | 1/2008 |

OTHER PUBLICATIONS

Matsue, H., "Prompt Gamma Ray Analysis Method Using Neutron Resonance Absorption," Database of Radiation Applications, Radiation Technique, Paper 47, Total 4 Pages, (Feb. 21, 2003) (with partial English translation).
(Continued)

*Primary Examiner* — David Porta
*Assistant Examiner* — Djura Malevic
(74) *Attorney, Agent, or Firm* — Oblon, McClelland, Maier & Neustadt, L.L.P.

(57) ABSTRACT

A method of non-destructive inspection of a subject body including an element is comprised of irradiating the subject body with a neutron ray through a first measurement point and a second measurement point; measuring an elapsed time after a first time point when a resonant neutron specific to the element passes through the first measurement point and before a second time point when a prompt gamma ray made emitted by the resonant neutron from the subject body is detected at the second measurement point; and determining a location of the element in the subject body by the first measurement point, the second measurement point, a relative position toward a surface of the subject body, and the elapsed time.

8 Claims, 5 Drawing Sheets

(56) References Cited

U.S. PATENT DOCUMENTS

| | | | |
|---|---|---|---|
| 4,864,142 A * | 9/1989 | Gomberg | 250/390.04 |
| 4,918,315 A * | 4/1990 | Gomberg et al. | 250/390.04 |
| 5,098,640 A | 3/1992 | Gozani et al. | |
| 5,142,153 A * | 8/1992 | Gomberg | 250/390.04 |
| 5,323,004 A * | 6/1994 | Ettinger et al. | 250/336.1 |
| 5,440,136 A * | 8/1995 | Gomberg | 250/390.04 |
| 5,539,788 A | 7/1996 | Ruddy et al. | |
| 5,818,054 A * | 10/1998 | Randers-Pehrson et al. | 250/390.04 |
| 6,909,764 B2 * | 6/2005 | Maksimchuk et al. | 376/190 |
| 7,027,555 B2 * | 4/2006 | Proctor | 378/57 |
| 7,286,635 B2 * | 10/2007 | Proctor | 378/57 |
| 7,405,409 B2 * | 7/2008 | Kearfott | 250/390.04 |
| 8,080,808 B2 * | 12/2011 | Norris | 250/390.04 |
| 8,217,360 B2 * | 7/2012 | Nukatsuka et al. | 250/370.11 |
| 8,288,734 B2 * | 10/2012 | Norris | 250/390.04 |
| 8,314,394 B1 * | 11/2012 | Penny et al. | 250/363.03 |
| 8,410,451 B2 * | 4/2013 | Norris | 250/393 |
| 8,426,822 B1 * | 4/2013 | Penny et al. | 250/363.03 |
| 8,586,939 B2 * | 11/2013 | Bingham et al. | 250/390.02 |
| 2004/0141585 A1 * | 7/2004 | Proctor | 378/57 |
| 2006/0093087 A1 * | 5/2006 | Procter | 378/57 |
| 2006/0126773 A1 * | 6/2006 | Haruyama | 376/159 |
| 2007/0069145 A1 * | 3/2007 | Leonhardt | 250/390.04 |
| 2008/0017806 A1 * | 1/2008 | Norris | 250/390.04 |
| 2008/0156997 A1 * | 7/2008 | Kearfott | 250/390.04 |
| 2010/0061500 A1 * | 3/2010 | Lou et al. | 376/114 |
| 2010/0065727 A1 * | 3/2010 | Choi | 250/251 |

OTHER PUBLICATIONS

International Search Report Issued Nov. 16, 2010 in PCT/JP10/67973 Filed Oct. 13, 2010.

U.S. Appl. No. 13/501,589, filed Apr. 12, 2012, Nose, et al.

Japanese Office Action Issued Apr. 23, 2013 in Patent Application No. 2009-238317 (with English translation).

Kodai Yamada et al., "Study on Non-Destructive Measurement of Concentrations of Chloride Ions in Concrete by Means of Prompt Gamma Ray Analysis", Concrete Research and Technology, vol. 31, No. 1, Jul. 2009, 9 pages with English summary and cover page.

* cited by examiner $$t_2 - t_0 = \frac{L + d}{v} \Rightarrow d = (t_2 - t_0) \cdot v - L$$

NON-DESTRUCTIVE INSPECTION METHOD AND DEVICE

TECHNICAL FIELD

The present invention relates to a method and a device of non-destructive inspection by which a state of a subject body is inspected without destroying the subject body.

BACKGROUND ART

As inspection of states (corrosion, cracks, cavity formation, or such) of structures or components, a visual inspection, a hammering test, an ultrasonic inspection (echo inspection) and such have been applied so far. The visual inspection and the hammering test are, however, likely to cause variations in inspection results depending on skill levels of inspectors, and inherently have limited inspection accuracy. These inspection methods are, in addition, applicable only to parts where workers can observe or hammer. While the ultrasonic inspection may not cause issues led from artificial inspection as discussed above, there is a difficulty in determination of locations.

There are proposed some inspection methods having accuracy, which utilize radiation. The non-patent literature as described below discloses an analysis method using a prompt gamma ray. The term "prompt gamma ray" generally means a ray emitted by a nuclear reaction within a very short time, but is herein particularly defined as a gamma ray emitted just after trapping of an epithermal neutron by resonance absorption.

CITATION LIST

Non Patent Literature

[NPL 1]: PROMPT GAMMA RAY ANALYSIS METHOD USING NEUTRON RESONANCE ABSORPTION (Database of Radiation Applications, Radiation Technique, 047 Paper, http://www.rada.or.jp/database/home4/normal/ht-docs/member/synopsis/040275.html)

DISCLOSURE OF INVENTION

According to the aforementioned analysis method using a prompt gamma ray, relatively small subject bodies can be inspected without destroying them. In cases where subject bodies are relatively large, however, the method requires to cut out some test pieces from the subject bodies. Thus the analysis using a prompt gamma ray has difficulty in execution as a non-destructive inspection method.

The present invention has been achieved in view of the aforementioned issues and is intended to provide a non-destructive inspection method without constraints about a shape of a subject body and locations of contained substances, and a non-destructive inspection device preferably applicable to the method, for the purpose of accurate inspection of states of the subject body.

According to a first aspect of the present invention, a method of non-destructive inspection of a subject body including an element is comprised of the steps of irradiating the subject body with a neutron ray through a first measurement point and a second measurement point, measuring an elapsed time after a first time point when a resonant neutron specific to the element passes through the first measurement point and before a second time point when a prompt gamma ray made emitted by the resonant neutron from the subject body is detected at the second measurement point, and determining a location of the element in the subject body by the first measurement point, the second measurement point, a relative position toward a surface of the subject body, and the elapsed time.

According to a second aspect of the present invention, a device of non-destructive inspection of a subject body including an element is comprised of a neutron ray source having a first measurement point and a second measurement point, the neutron ray source being so positioned as to irradiate the subject body with a neutron ray through the first measurement point and the second measurement point, a resonant neutron detector for detecting a first time point when a resonant neutron specific to the element passes through the first measurement point, the resonant neutron detector being disposed at the first measurement point, a gamma ray detector for detecting a prompt gamma ray made emitted by the resonant neutron from the subject body is detected at the second measurement point, the gamma ray detector being disposed at the second measurement point, a measurement device configured to measure an elapsed time after the first time point and before the second time point when the prompt gamma ray, the measurement device being electrically connected with the resonant neutron detector and the gamma ray detector, and a controller for calculating a location of the element in the subject body from the first measurement point, the second measurement point, a relative position toward a surface of the subject body, and the elapsed time.

BEST MODE FOR CARRYING OUT THE INVENTION

Certain embodiments will be described hereinafter with reference to the appended drawings.

Figure 1:
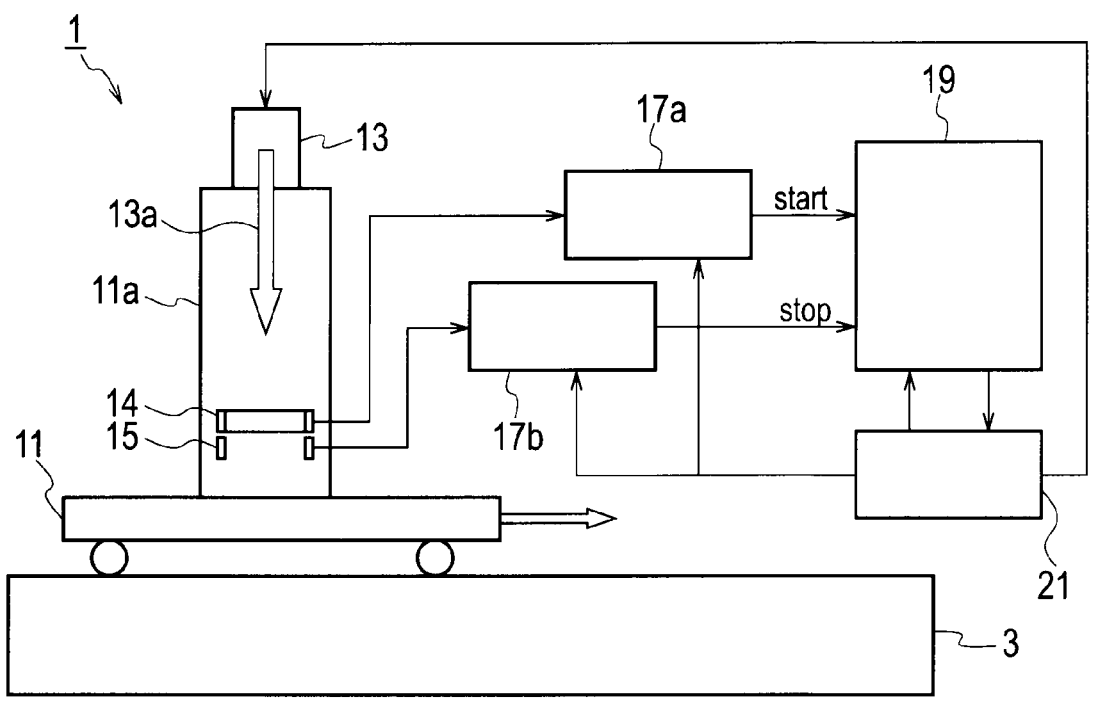
FIG. 1 is a block diagram of a non-destructive inspection device in accordance with an embodiment of the present invention.

FIG. 1 illustrates an outline of a non-destructive inspection device in accordance with an embodiment of the present invention.

The non-destructive inspection device 1 utilizes a phenomenon that an atomic nucleus capturing a neutron emits a prompt gamma ray, and inspects a state of a subject body by detecting a prompt gamma ray from the subject body which is irradiated with a neutron. Descriptions will be given hereinafter in regard to an example in which reinforced concrete 3 constituting a bridge or such is a subject body and inspection is carried out in order to know a state of corrosion by a chloride attack. The subject of inspection is a distribution of a reinforcing bar in the reinforced concrete 3 and a distribution of chlorine (or chloride ion) that causes the chloride attack.

The non-destructive inspection device 1 of the present embodiment is comprised of a mobile pedestal 11 movable on the reinforced concrete 3, a neutron ray source 13 for outputting a neutron ray, a resonant neutron detector 14 for detecting a resonant neutron corresponding to a particular element in a neutron ray, and a gamma ray detector 15 for detecting a prompt gamma ray from the reinforced concrete 3. The neutron ray source 13, the resonant neutron detector 14, and the gamma ray detector 15 are set up on the mobile pedestal 11.

The non-destructive inspection device 1 of the present embodiment is comprised of a wave height analyzer 17a connected with the resonant neutron detector 14, a wave height analyzer 17b connected with the gamma ray detector 15, an elapsed time measurement device 19 connected with both the wave height analyzers 17a,17b for measuring a time difference between signals therefrom, and a controller 21 for controlling them. The wave height analyzer 17a measures the prompt gamma ray in accordance with the output from the resonant neutron detector 14. The wave height analyzer 17b measures the prompt gamma ray in accordance with the output from the gamma ray detector 15. The measurement device 19 is capable of setting thresholds in regard to the respective outputs of the wave height analyzers 17a,17b, and measures an elapsed time between time points when signals over the thresholds are input.

To the mobile pedestal 11 applicable is any cart movable on the reinforced concrete 3. Alternatively a self-propelled cart having a drive source may be applied thereto. Meanwhile it is preferable that a position (position on the reinforced concrete 3 where irradiated with a neutron ray by the neutron ray source 13) of the mobile pedestal 11 on the reinforced concrete 3 is continuously grasped by the controller 21, even whether the mobile pedestal 11 is self-propelled or driven. One of axles of the mobile pedestal 11 may be, for example, comprised of a revolution counter to allow the controller 21 to integrate the output of the revolution counter, thereby grasping the position. Alternatively the mobile pedestal 11 may be comprised of a distance meter, an acceleration meter, or a position sensor instead of the revolution counter.

Figure 2:
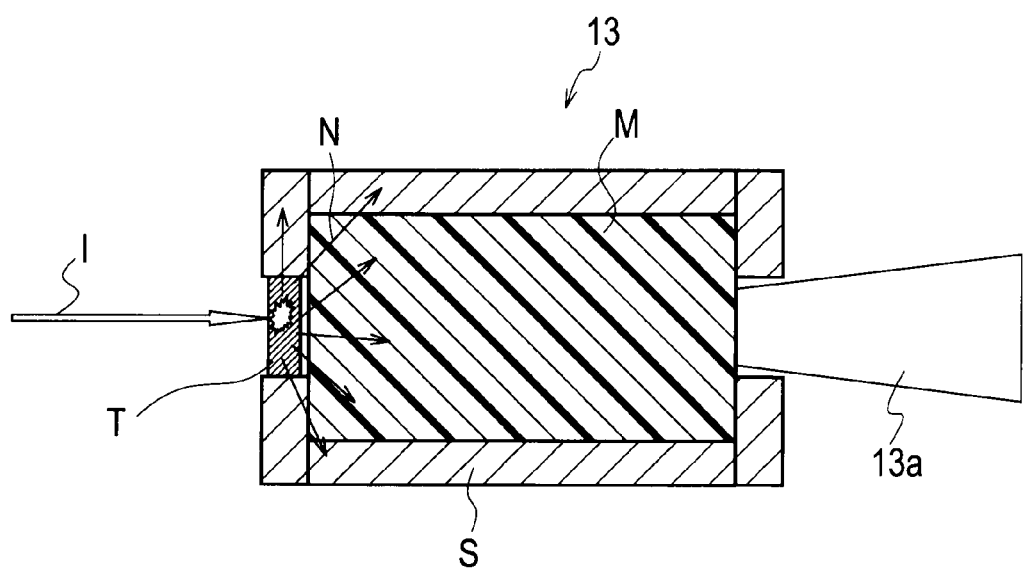
FIG. 2 is an explanatory drawing depicting a principle of generating a neutron ray at a neutron ray source of FIG. 1.

To the neutron ray source 13 applicable is any one known in the art. The neutron ray source 13 as shown in FIG. 2 is, for example, comprised of a target T to be irradiated with ions I, a moderating material M for moderating or slowing down fast neutrons N, and a protective wall S for protecting the fast neutrons N and the moderating material M from the exterior. The target T includes materials such as Be or $^2$H so as to effectively generate neutrons from ions I such as H, $^2$H or $^4$He emitted from an external ion generator. The moderating material M is formed of any proper material, such as polyethylene, heavy water, or light water for example, to moderate or slow down the fast neutrons N generated in the target T. The fast neutrons N are converted into a neutron ray 13a having a continuous spectrum including thermal neutrons (0.5 eV or less) and epithermal neutrons (0.5-$10^3$ eV) by the moderating material M. The proper moderator protective wall S encapsulates the moderating material M and also prevents the fast neutrons N from leaking out. Further one end of the protective wall S (normally the opposite side to the target) opens to radiate the neutron ray 13a therethrough to the exterior. The neutron ray source 13 is set up on an upper portion of a protective body 11a of a chamber-like form set up on the mobile pedestal 11. The neutron ray 13a output from the neutron ray source 13 (see FIG. 1) passes through the interior of the protective body 11a and the mobile pedestal 11 and is emitted onto the reinforced concrete 3 in a direction of a normal line relative to its surface.

Figure 3:
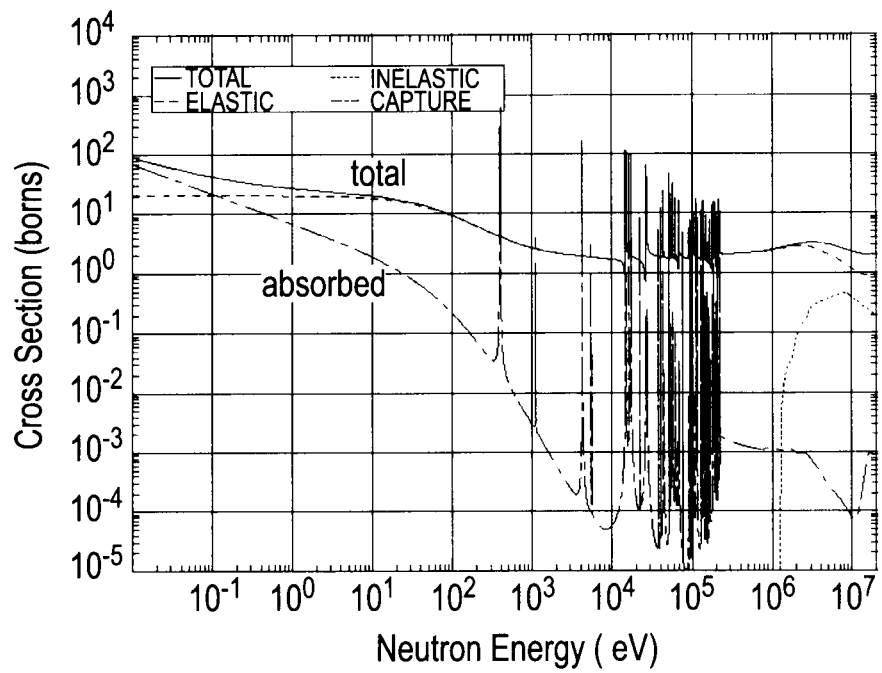
FIG. 3 is a graph depicting a relation between a neutron energy and a capture cross-section in regard to chlorine 35.
Figure 4:
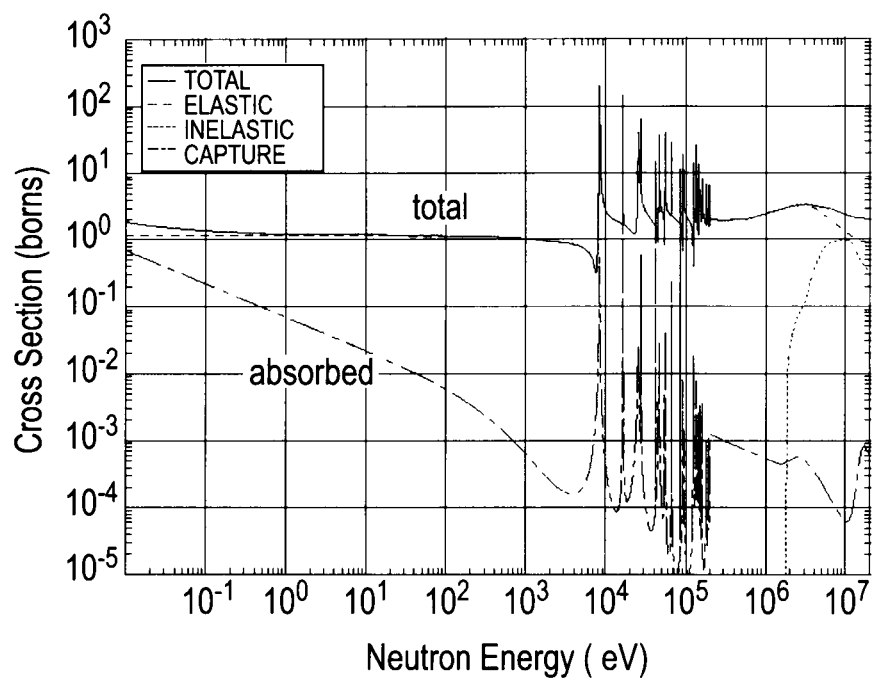
FIG. 4 is a graph depicting a relation between a neutron energy and a capture cross-section in regard to chlorine 37.

When an atomic nucleus is irradiated with the neutron ray 13a including epithermal neutrons, resonant absorption of neutrons having energies specific to the atomic nucleus occurs. A neutron subject to resonant absorption into an atomic nucleus is referred to as a resonant neutron. The graphs of FIG. 3 and FIG. 4 show relations between energies of emitted neutrons and capture cross sections in regard to chlorine 35 and chlorine 37, respectively. As will be understood if FIG. 3 (chlorine 35) is compared with FIG. 4 (chlorine 37), acknowledged are sharp peaks compared with adjacent energy regions in a capture cross section curve, which are at a specific neutron energy region around $10^2$-$10^3$ eV and corresponding to epithermal neutrons. More specifically, there are neutrons specifically subject to resonant absorption into chlorine 35 (these are distinct from those of chlorine 37), which are referred to as "resonant neutrons" hereinafter. Use of the resonant neutrons enables discrimination of chlorine 35 from chlorine 37 by determining whether the subject absorbs the resonant neutrons or not. Throughout the present specification and the appended claims, the term "resonant neutron" is defined and used as a meaning of "a neutron among neutrons included in a neutron ray with a continuous spectrum, which has an energy corresponding to a resonant level specific to an element, thereby being resonantly absorbed into the element".

An atomic nucleus capturing a resonant neutron by resonant absorption emits a prompt gamma ray. The energy of the prompt gamma ray differs in accordance with the neutron energy of the resonant neutron captured by the atomic nucleus. Therefore an energy of a prompt gamma ray emitted by a nucleus is specific to the nucleus. By utilizing this principle, the non-destructive inspection device 1 of the present embodiment analyzes a distribution of elements (in particular, iron used as a reinforcing bar, and chlorine as chloride ion) contained in the reinforced concrete 3. For this purpose, in the non-destructive inspection device 1, a neutron ray 13a as epithermal neutrons emitted from the neutron ray source 13 is emitted onto the reinforced concrete 3 and a prompt gamma ray emitted from (particular elements contained in) the reinforced concrete is detected by the gamma ray detector 15. Further, passage of resonant neutrons of specific elements included in the neutron ray 13a from the neutron ray source 13 is detected by the resonant neutron detector 14.

Figure 5:
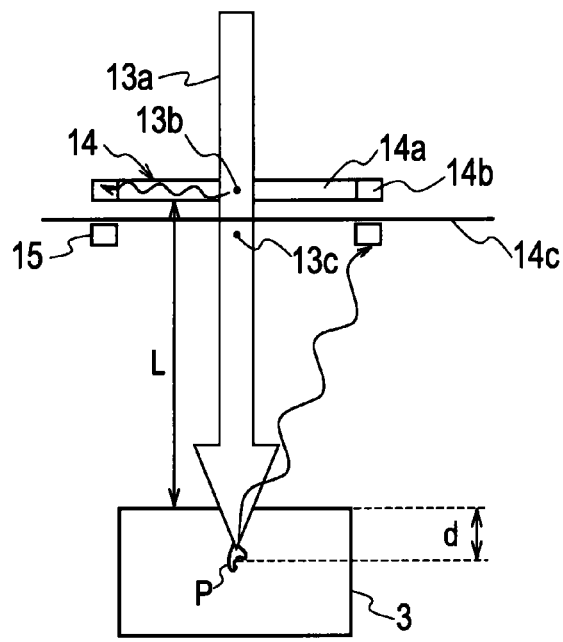
FIG. 5 is an explanatory drawing depicting a principle of location analysis of chlorine by means of the non-destructive inspection device of FIG. 1.

The resonant neutron detector 14 is, as shown in FIG. 1, housed in the protective body 11 on the mobile pedestal 11. Further the resonant neutron detector 14 is, as shown in FIG. 5, disposed at a reference point 13b on an irradiation axis line of the neutron ray 13a from the neutron ray source 13. This reference point 13b is set at a point distant away from a surface of the reinforced concrete 3 by a distance L.

The resonant neutron detector 14 has a neutron monitor 14a and a circular gamma ray monitor 14b disposed around the neutron monitor 14a.

Figure 6:
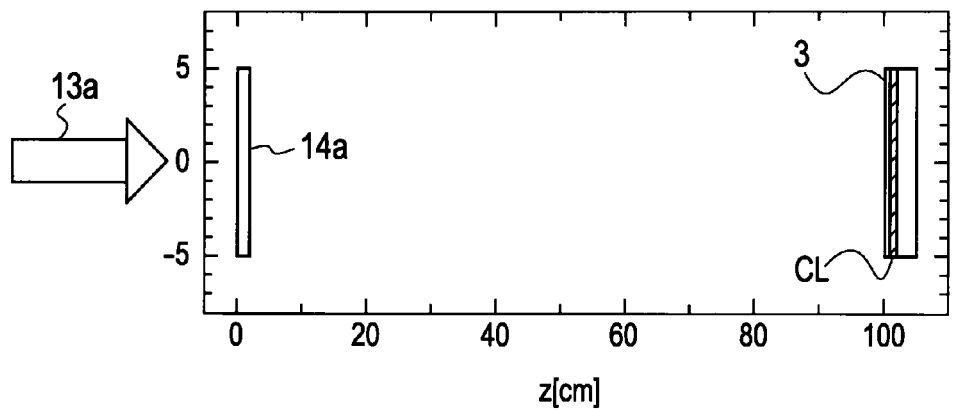
FIG. 6 is an explanatory drawing depicting a principle of detecting passage of a resonant neutron by means of a resonant neutron monitor of FIG. 5.

The neutron monitor 14a is to monitor a neutron ray 13a passing through the reference point 13b and is a target of a thin plate made of a material including any specific element (or its compound) contained in the reinforced concrete 3. In a case where a distribution of chlorides in the reinforced concrete 3 is measured for example, the specific element is chlorine and thus the neutron monitor 14a is preferably a thin plate of calcium chloride ($CaCl_2$) or a container filled with carbon tetrachloride. Further in a case where a distribution of iron bar in the reinforced concrete is measured, the specific element is iron and thus the neutron monitor 14a is preferably a thin plate of iron or its compound. FIG. 6 shows a positional relation between the neutron monitor 14a and the reinforced concrete 3.

To the gamma ray monitor 14a applicable is any gamma ray sensor known in the art. A scintillation detector comprised of a scintillator that receives a gamma ray to emit fluorescent light, and a photomultiplier tube or a photodiode that measures intensity of this fluorescent light is applicable. Alternatively a known semiconductor detector can be used.

In accordance with the resonant neutron detector 14 constituted in a way described above, as shown in FIG. 5, the specific element contained in the neutron monitor 14a captures a resonant neutron in the neutron ray 13a to output a prompt gamma ray when the neutron ray 13a emitted from the neutron ray source 13 passes through the neutron monitor 14a. Further the prompt gamma ray is detected by the gamma ray monitor 14b. Thus a time point when the gamma ray monitor 14b detects the prompt gamma ray from the neutron monitor 14a is acknowledged as a time point when the resonant neutron in the neutron ray 13a passes through the resonant neutron detector 14, namely a time point when the neutron ray source 13 outputs the neutron ray 13a including the resonant neutron.

Disposed between the resonant neutron detector 14 and the gamma ray detector 15 is a gamma ray shield 14c. By means of the gamma ray shield 14c, passage of the prompt gamma ray from the neutron monitor 14a to the gamma ray detector 15 is obstructed. As the gamma ray shield 14c, a plate of any heavy metal such as iron, lead, bismuth or tungsten, or any compound thereof, can be exemplified, or alternatively an article in which such a plate is put between glasses or such is applicable. The gamma ray shield 14c may have an opening along an irradiation axis in order to allow passage of neutrons.

The gamma ray detector 15 along with the resonant neutron detector 14 is, as shown in FIG. 1, housed in the protective body 11a. The gamma ray detector 15 is, as shown in FIG. 5, disposed at a measurement point 13c slightly closer to the reinforced concrete 3 as compared with the reference point 13b. The gamma ray detector 15 is, as with the gamma ray monitor 14b, circular and a known sensor such as a scintillation detector or a semiconductor detector may be applied thereto.

In accordance with the gamma ray detector 15 constituted in a way described above, a prompt neutron which the specific element contained in the reinforced concrete 3 irradiated with the neutron ray 13a captures a resonant neutron to emit is detected. As shown in FIG. 6, the reinforced concrete 3 has a layer CL containing chlorine of 4 weight % therein. FIG. 5 shows an example in which the non-destructive inspection device 1 detects chlorides in a case where the chlorides exist at a particular location P in the reinforced concrete 3.

As the resonant neutron detector 14 and the gamma ray detector 15 have the aforementioned positional relation, a time difference (elapsed time) between a time point of output of the neutron ray 13a from the neutron ray source 13, which is detected by the resonant neutron detector 14, and a time point of detection of the prompt gamma ray from the specific element contained in the reinforced concrete 3, which is detected by the gamma ray detector 15, can be measured by the measurement device 19. Further, from the measured elapsed time, the controller 21 can specify a location of the particular location P in the reinforced concrete 3 emitting the prompt gamma ray by means of a TOF method as described later.

In the meantime, a travel speed of a gamma ray is far greater than a travel speed v of a neutron. Therefore, as compared with an elapsed time after a time point $t_0$ when the neutron ray 13a passes through the resonant neutron detector and before a time point $t_1$ when the neutron ray 13a reaches the particular location P, an elapsed time after the time point $t_1$ and before a time point $t_2$ when the gamma ray emitted from the specific element in the reinforced concrete 3 is detected by the gamma ray detector 15 at the measurement point 13c is far shorter. Therefore the aforementioned time difference (elapsed time $t_2-t_0$) can be regarded to be equal to the elapsed time ($t_1-t_0$) after the time point $t_0$ and before the time point $t_1$.

Therefore, in accordance with the TOF method, the depth of the particular location P containing the specific element contained in the reinforced concrete 3 can be determined in a way as described below. More specifically, as the elapsed time ($t_2-t_0$) is equal to the elapsed time ($t_1-t_0$) and a distance that the neutrons of the neutron ray 13a travels is (L+d), $t_2-t_0=(L+d)/v$. This equation can be, if rewritten, represented as $d=(t_2-t_0)v-L$, where $t_0$ is a time point when the neutron ray 13a including the resonant neutrons corresponding to the specific element passes through the resonant neutron detector 14, $t_2$ is a time point when the prompt gamma ray from the specific element contained in the reinforced concrete 3 is detected by the gamma ray detector 15, v is a travel speed of the neutron ray 13a including the resonant neutron, and d is a depth of the particular location P containing the specific element from the surface of the reinforced concrete 3.

The respective wave height analyzers 17a,17b, when being triggered by the controller 21 in synchronization with output of the neutron ray 13a from the neutron ray source 13, decompose gamma rays respectively detected by the correspondent gamma ray monitor 14b and the correspondent gamma ray detector 15 into components on the basis of a plurality of energy ranges and then measures these intensities. Further, as an intensity of the gamma ray in a specific energy range where the intensity rises according to a specific element is confirmed, the controller 21 determines whether the gamma ray detected by the gamma ray monitor 14b or the gamma ray detector 15 is a prompt gamma ray from the specific element in the reinforced concrete 3 or not. Where it is determined to be a prompt gamma ray, the wave height analyzer 17a outputs a start signal and the wave height analyzer 17b outputs a stop signal, respectively.

Figure 7:
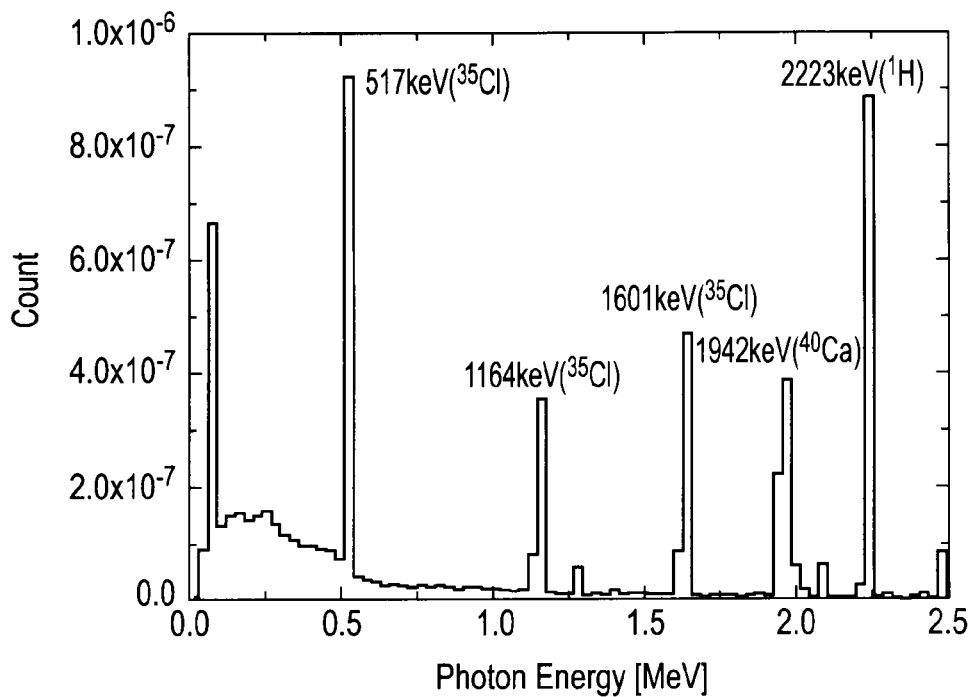
FIG. 7 is a graph depicting an energy spectrum of a gamma ray emitted from calcium chloride.

Specific energy ranges where existence of a specific element causes an intensity of a gamma ray to rise, when reviewing an energy spectrum of a gamma ray emitted from calcium chloride for example, show peaks around 517 keV, 1164 keV, and 1601 keV as shown in FIG. 7, which originate from peaks of energy of a prompt gamma ray from chlorine 35. Therefore, by confirming whether a peak of energy exists in a gamma ray detected by the gamma ray monitor 14b or the gamma ray detector 15 in the energy range including (any of) these peaks or not from intensity of a gamma ray in an energy range corresponding to that decomposed by the wave height analyzers 17a,17b, it can be determined whether the gamma ray is a prompt gamma ray from a specific element or not. As discussed above, determination can be executed by whether the intensity exceeds a threshold set in advance.

Figure 8:
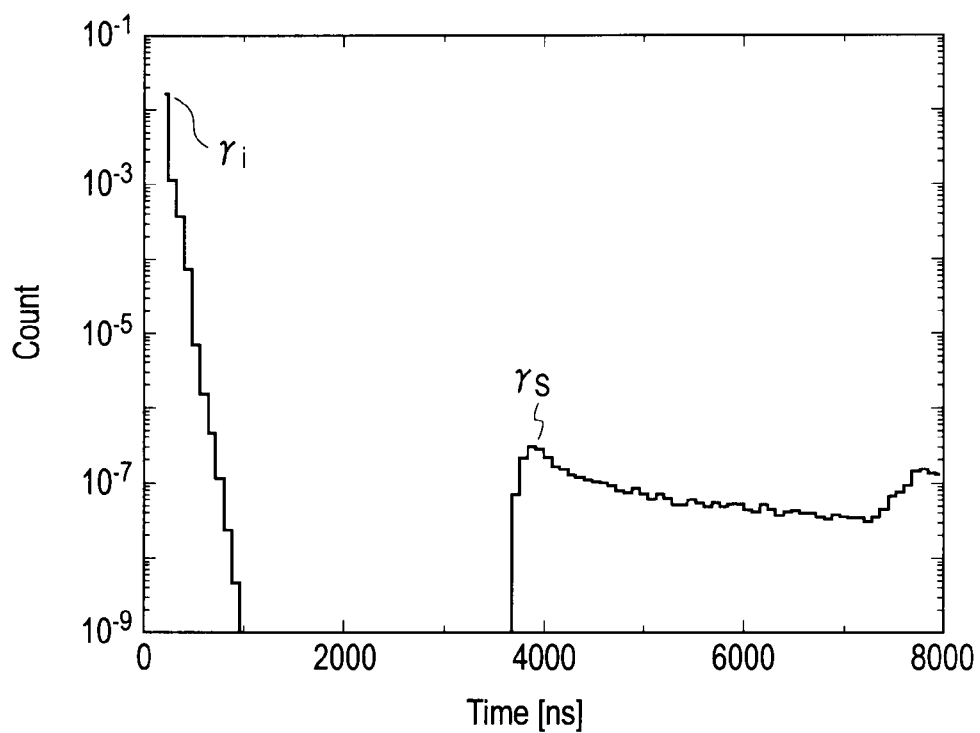
FIG. 8 is a graph depicting a time spectrum of a gamma ray generated at the time of distribution inspection of chlorine or chloride ion in reinforced concrete by means of the non-destructive inspection device of FIG. 1.

In the meantime, in a space where the non-destructive inspection device 1 is set up, a prompt gamma ray is for a very short time generated as shown by a curve $\gamma_t$ in the graph of FIG. 8 at a time point just after output of the neutron ray 13a from the neutron ray source 13 as a resonant neutron in the neutron ray 13a passes through the neutron monitor 14a of the resonant neutron detector 14. As the time it takes the neutron ray 13a to get incident on the reinforced concrete 3 passes thereafter, a prompt gamma ray is radiated as shown by a curve $\gamma_s$ in the drawing from an element contained in the reinforced concrete, which captures the resonant neutron in the neutron ray 13a.

Generation of the prompt gamma ray from the reinforced concrete 3 continues for a certain time as shown by part $\gamma_s$ beyond about 4000 ns of the abscissa axis of the graph of FIG. 8. This is caused by a phenomenon that the specific element contained in the reinforced concrete 3 keeps to generate prompt gamma rays as epithermal neutrons contained in the neutron ray 13a are kept decelerated in the reinforced concrete 3 and thus epithermal neutrons kept generated are captured by the specific element in the reinforced concrete 3.

Therefore it is required to discriminate part of an energy spectrum of a prompt gamma ray radiated by a specific element from a gamma ray energy spectrum beyond 400 ns in the graph of FIG. 8 detected by the gamma ray detector 15 when a prompt gamma ray from the specific element in the reinforced concrete 3 is sought to be detected by the gamma ray detector 15. So the wave height analyzer 17b corresponding to the gamma ray detector 15 executes a process of subtracting an energy spectrum of a gamma ray detected by the gamma ray detector 15 in a case where the neutron ray 13a is emitted onto a target without the specific element from the energy spectrum of the gamma ray detected by the gamma ray detector 15. Solely an energy spectrum specific to the prompt gamma ray radiated from the specific element can be thereby extracted from detected signals of the gamma ray detector 15. Rising part of time in the extracted energy spectrum is then specified. At a time point when the rising part is detected, the wave height analyzer 17b outputs a stop signal.

Figure 9:
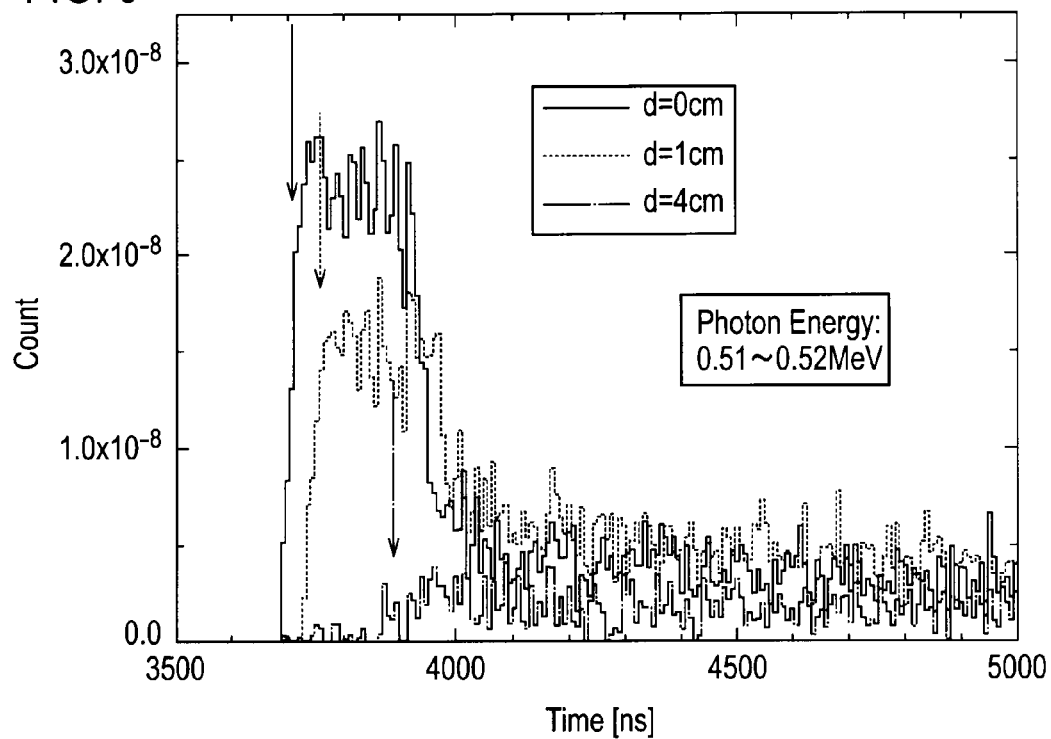
FIG. 9 is a graph depicting results of simulations about some depths into reinforced concrete, in which energy spectra of a prompt gamma ray from chlorine in the reinforced concrete are drawn.

FIG. 9 shows results each simulating an energy spectrum of a prompt gamma ray from chlorine in a reinforced concrete 3 extracted from detected signals of the gamma ray detector 15 depending on its depth d in the reinforced concrete 3. As shown in FIG. 9 with some variants in line forms, the simulation results, where depths d of a specific element in the reinforced concrete 3 are 0, 1, 4 (cm), commonly show that rising parts in the energy spectra of the prompt gamma rays can be specified.

As shown in FIG. 1, the measurement device 19, as triggered by the controller 21 in synchronization with output of the neutron ray 13a from the neutron ray source 13, measures an elapsed time after input of the start signal from the wave height analyzer 17a and before input of the stop signal from the wave height analyzer 17b.

The controller 21 calculates a location of the specific element (a depth d from a surface of the reinforced concrete 3) in the reinforced concrete 3 irradiated with the neutron ray 13a from the neutron ray source 13 on the basis of the elapsed time measured by the measurement device 19 by utilizing the aforementioned equation.

As will be apparent from the above discussion, in the non-destructive inspection device 1 of the present embodiment, a resonant neutron detection means is constituted of the resonant neutron detector 14 and the wave height analyzer 17a. Further in the non-destructive inspection device 1 of the present embodiment, a prompt gamma ray detection means is constituted of the gamma ray detector 15 and the wave height analyzer 17b.

In inspection of the reinforced concrete 3 with using the non-destructive inspection device 1 of the present embodiment as constituted as above, a location of the mobile pedestal 11 on the reinforced concrete 3, in other words an irradiated location of the reinforced concrete 3 with the neutron ray 13a, is changed throughout the whole surface of the reinforced concrete 3, like a matrix for example, in each cycle.

Then at each location irradiated with the neutron ray 13a, the following steps (1) through (5) are executed. More specifically, the method of non-destructive inspection is comprised of:

(1) radiating a neutron ray 13a from a neutron ray source 13 toward a reinforced concrete 3 to cause a nucleus of an element contained in the reinforced concrete 3, which captures a neutron in the neutron ray 13a, to emit a prompt gamma ray;

(2) detecting a time point when the neutron ray 13a containing a resonant neutron is output from the neutron ray source 13 and then radiated toward the reinforced concrete 3, by means of a resonant neutron detector 14 and a wave height analyzer 17a disposed at a reference point 13b on an irradiation axis line of the neutron ray 13a;

(3) detecting a time point when the prompt gamma ray that the specific element in the reinforced concrete 3 captures the resonant neutron to emit is detected at a measurement point 13c by the gamma ray detector 15 disposed at the measurement point 13c just close to the reference point 13b, by means of a wave height analyzer 17b;

(4) measuring an elapsed time after the time point when the neutron ray 13a including the resonant neutron is output from the neutron ray source 13 and radiated toward the reinforced concrete 3 and before the time point when the prompt gamma ray that the specific element in the reinforced concrete 3 captures the resonant neutron and then emits is detected at the measurement point 13c; and (5) detecting a location of the specific element in the reinforced concrete 3, namely a depth d from a surface of the reinforced concrete 3 at part irradiated with the neutron ray 13a, on the basis of the measured elapsed time and relative positions of the reference point 13b and the measurement point 13c on the neutron ray 13a relative to the reinforced concrete 3.

As described above, the series of the steps are repeatedly executed with moving the non-destructive inspection device 1 to change its position.

In each cycle of inspection as described above, if a prompt gamma ray is radiated from a nucleus of a specific element existing at a depth d from a surface of the reinforced concrete 3, it is detected by the gamma ray detector 15. Therefore, if the aforementioned cycle of inspection is executed, analysis of the specific element in the reinforced concrete 3 is carried out throughout the surface direction and the depth direction of the reinforced concrete 3.

Meanwhile, in a case where a distribution of iron (reinforcing bar) in the reinforced concrete 3 is inspected by means of the non-destructive inspection device 1 of the present embodiment, as the neutron monitor 14a of the resonant neutron detector 14, a target including iron or any iron compound is applied instead of a thin plate of calcium chloride for inspecting a distribution of chlorine. Alternatively, if any other target is applied, a distribution of any other element can be inspected.

After inspecting the distribution of iron (reinforcing bar) and the distribution of chlorine (chloride ion) in the reinforced concrete 3 respectively, the controller 21 analyzes a state of corrosion (existence or non-existence of corrosion, possibility of corrosion occurrence, expected time of corrosion occurrence or such) on the basis of how the distribution of the iron (reinforcing bar) is close to the distribution of chlorine (chloride ion) in the reinforced concrete 3.

Thus, by applying a material including a specific element or its compound of the subject of inspection of its distribution to the neutron monitor 14a of the resonant neutron detector 14, non-destructive inspection of the distribution of the specific element in the reinforced concrete 3 can be carried out.

As described above, in accordance with the non-destructive inspection device 1 of the present embodiment, as successively changing part of the reinforced concrete 3 irradiated with the neutron ray 13a in its surface direction and depth direction totally, and detecting an energy spectrum specific to an element from a prompt gamma ray emitted along with capture of a resonant neutron by a nucleus of the specific element in the reinforced concrete 3, existence or non-existence of the specific element in the reinforced concrete 3 can be analyzed by destructive inspection.

Meanwhile in the present embodiment, the elapsed time after the time point $t_0$ when the neutron ray 13a including the resonant neutron passes through the resonant neutron detector 14 and before the time point $t_2$ when the prompt gamma ray from the specific element in the reinforced concrete 3 is detected by the gamma ray detector 15 is made measurable by the time lag therebetween. The elapsed time after the time point $t_0$ and before the time point $t_2$ may be measured by a difference in elapsed times after a third time point and before the respective time points $t_0$, $t_2$.

Figure 10:
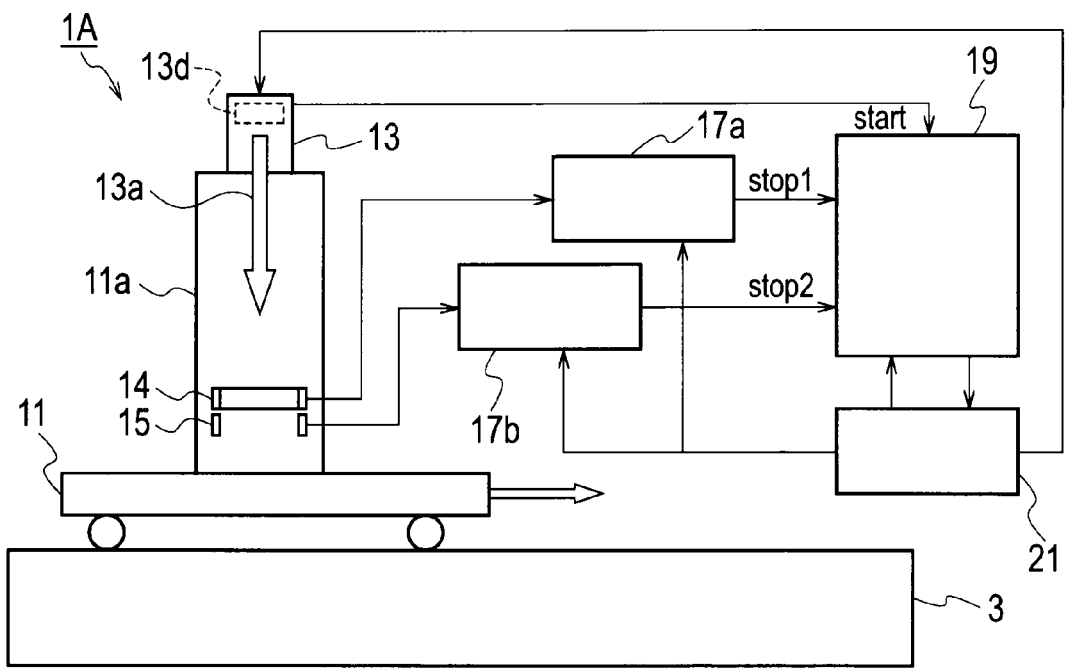
FIG. 10 is a drawing of a general construction depicting a non-destructive inspection device in accordance with other embodiment of the present invention.

One constituted in the aforementioned way is a non-destructive inspection device of another embodiment of the present invention shown in FIG. 10. The non-destructive inspection device of the present embodiment as indicated by a reference sign 1A in FIG. 10 is modified in that the start signal and the stop signal output from the respective wave height analyzer 17a,17b in the non-destructive inspection device 1 of the embodiment shown in FIG. 1 are modified into a first stop signal and a second stop signal respectively. Further the neutron ray source 13 is comprised of an irradiation detector. The irradiation detector is constituted of an ion monitor 13d interposed between an ion generator and a target (see FIG. 2), and is electrically connected with the measurement device 19. The ion monitor 13d is to detect passage of ions to output it as an electric signal, and, as the ion monitor 13d, a known ionization chamber comprised of a pair of electrodes and gas filled in therebetween can be exemplified. Instead of the ionization chamber, a proportional counter tube or a scintillation detector may be applied thereto. Alternatively, without using the ion monitor, any detection means capable of detecting a time point when the neutron ray source 13 radiates the neutron ray 13a may be applied.

According to the non-destructive inspection device 1A, the neutron ray source 13 instead of the wave height analyzer 17a outputs a start signal to the measurement device 19 at a time point $t_0$ of radiating a neutron ray 13a toward the reinforced concrete 3. In other points, it is constituted in a way as with the non-destructive inspection device 1 of the embodiment shown in FIG. 1.

The time point $t_0$ when the neutron ray source 13 emits the neutron ray 13a to the reinforced concrete 3 may be set to be a time point when an ion radiated by a not shown ion generator to the target (see FIG. 2) is detected by the ion monitor 13d.

The measurement device 19 of the present embodiment, when being triggered in synchronization with the output of the neutron ray 13a from the neutron ray source 13, measures an elapsed time $(t_0-t_a)$ after input of a start signal from the neutron ray source 13 and before input of a first stop signal from the wave height analyzer 17a, and an elapsed time $(t_2-t_a)$ until input of a second stop signal from the wave height analyzer 17b. Further the measurement device 19, on the basis of the measured time differences among the respective elapsed times, calculates an elapsed time $(t_2-t_0)$ after a time point $t_0$ when the neutron ray 13a including a resonant neutron passes through the resonant neutron detector 14 and before a time point $t_2$ when a prompt gamma ray from a specific element contained in the reinforced concrete 3 is detected by the gamma ray detector 15.

Thus, also by the non-destructive inspection device 1A of the present embodiment, effects similar to those of the non-destructive inspection device 1 of the embodiment shown in FIG. 1 can be obtained. Further in accordance with the non-destructive inspection device 1A of the present embodiment, the time point $t_0$ when the neutron ray 13a including the resonant neutron passes through the resonant neutron detector 14 can be detected with more precision as compared with the non-destructive inspection device 1 shown in FIG. 1. Thus positions of specific elements in the reinforced concrete 3 that the controller 21 specifies by the TOF method can be made more precise. The reason will be described below.

More specifically, the time point $t_o$ when the neutron ray 13a including the resonant neutron passes through the resonant neutron detector 14 considerably varies in accordance with a distribution in neutron energy of a resonant neutron. Thus it is usually acknowledged that a time point in rising of the neutron energy of the resonant neutron is the time point $t_0$ when the neutron ray 13a including the resonant neutron passes through the resonant neutron detector 14.

If the time variation in the time point $t_0$ when the neutron ray 13a including the resonant neutron passes through the resonant neutron detector 14 is relatively large, however, a time point at the rising of the neutron energy of the resonant neutron would deviate wide in terms of time from a time point when the neutron energy of the resonant neutron passing through the resonant neutron detector 14 shows a peak, which is ideal as the time point $t_0$. If this deviation was relatively wide, the input timing (the time point $t_0$) of the start signal from the wave height analyzer 17a for the measurement device 19 of the non-destructive inspection device 1 of the embodiment shown in FIG. 1 to start measuring the elapsed time $(t_2-t_0)$ might have a considerable error.

This error leads to an error in a measured value of the elapsed time $(t_2-t_0)$, and further leads to an error in a position (a depth d) of a specific element contained in the reinforced concrete 3 detected on the basis of the elapsed time $(t_2-t_0)$.

Thus in the non-destructive inspection device 1A of the present embodiment, the time point of starting measurement of the elapsed time by the measurement device 19 is changed into the time point $t_a$ when the neutron ray source 13 radiates the neutron ray 13a toward the reinforced concrete 3. Further the signal that the wave height analyzer 17a outputs at the time point $t_0$ is used not as a start signal but as the first stop signal as with the stop signal (the second stop signal in the present embodiment) output from the wave height analyzer 17b at the time point $t_2$, and thus the time point $t_0$ is set to be a time point for finishing measurement of the elapsed time by the measurement device 19.

The wave height analyzer 17a thereby keeps outputting the stop signal periodically after the time point at the rising of the neutron energies of the resonant neutrons passing through the resonant neutron detector 14 until the neutron energy reaches a peak, or while it goes beyond the predetermined threshold. Therefore the measurement device 19 comes to measure the elapsed time after the time point $t_a$ when the neutron ray source 13 radiates the neutron ray 13a toward the reinforced concrete 3 and before the time point $t_0$ when the neutron ray 13a passes through the resonant neutron detector 14, for the same times as the number of the first stop signals output by the wave height analyzer 17a. Thus an ideal elapsed time $(t_0-t_a)$ in which the time point when the neutron energy of the resonant neutron passing through the resonant neutron detector 14 shows a peak can be selected from measured elapsed times $(t_0-t_a)$ by statistically analyzing the measured elapsed times $(t_0-t_a)$.

Thereby the elapsed time $(t_2-t_0)$ can be measured more precisely as compared with the measurement device 19 of the non-destructive inspection device 1 of the embodiment shown in FIG. 1 on the basis of a difference between the elapsed time $(t_2-t_a)$ after the time point $t_a$ when the neutron ray source 13 radiates the neutron ray 13a toward the reinforced concrete 3 and before the time point $t_2$ when the gamma ray emitted from the specific element in the reinforced concrete 3 is detected by the gamma ray detector 15 and the elapsed time $(t_0-t_a)$. Therefore the location of the specific element contained in the reinforced concrete 3 specified by the controller 21 on the basis of the TOF method can be determined more precisely.

Meanwhile, in the respective embodiments as described above, although an example in which the non-destructive inspection device 1,1A has the mobile pedestal 11 movable on the reinforced concrete 3 as its subject, the mobile pedestal 11 may be omitted.

Moreover, the non-destructive inspection device 1,1A may be modified to have a display means for visualizing and displaying locations of specific elements contained in a reinforced concrete 3 as analyzed in a way described above. In this case, there may be some ways of display by the display means. A data indicating an analysis result of a distribution of chlorine in a depth direction from a surface of the reinforced concrete 3 and a direction of travel of the mobile pedestal 11 can be displayed by a form of contour lines corresponding to concentrations of chlorine, or by a form of shades of indication. Constitutions in which analysis results are visualized and displayed on site are helpful for quick grasp of the analysis results on site where non-destructive inspection of the reinforced concrete 3 is executed.

INDUSTRIAL APPLICABILITY

A non-destructive inspection method without constraints about a shape of a subject body and locations of contained substances, and a non-destructive inspection device preferably applicable to the method, are provided.

The invention claimed is:

1. A method of non-destructive inspection of a subject body including an element, comprising the steps of:
  irradiating the subject body with a neutron ray through a first measurement point, the first measurement point being a point distinct from a position of a source of the neutron ray;
  measuring an elapsed time from a first time point when a resonant neutron specific to the element passes through the first measurement point to a second time point when a prompt gamma ray emitted by the resonant neutron from the subject body is detected at a second measurement point distinct from the first measurement point; and
  determining a location of the element in the subject body by the first measurement point, the second measurement point, a relative position toward a surface of the subject body, and the elapsed time.

2. The method of claim 1, further comprising:
  detecting the first time point by detecting a gamma ray emitted from a target including the element positioned at the first measurement point.

3. The method of claim 1, further comprising:
  detecting the second time point by a gamma ray detector disposed at the second measurement point.

4. The method of claim 1, wherein the respective steps are executed as positions where the neutron ray is irradiated are sequentially changed.

5. A device of non-destructive inspection of a subject body including an element, comprising:
  a neutron ray source positioned as to irradiate the subject body with a neutron ray through a first measurement point, the first measurement point being a point distinct from the position of the neutron ray source;
  a resonant neutron detector for detecting a first time point when a resonant neutron specific to the element passes through the first measurement point, the resonant neutron detector being disposed at the first measurement point;
  a gamma ray detector for detecting a second time point when a prompt gamma ray emitted by the resonant neutron from the subject body is detected at a second measurement point, the gamma ray detector being disposed at the second measurement point;
  a measurement device configured to measure an elapsed time from the first time point to the second time point, the measurement device being electrically connected with the resonant neutron detector and the gamma ray detector; and
  a controller for calculating a location of the element in the subject body from the first measurement point, the second measurement point, a relative position toward a surface of the subject body, and the elapsed time.

6. The device of claim 5, further comprising:
  an irradiation detector configured to detect irradiation of the neutron ray onto the subject body, wherein the measurement device is configured to measure the elapsed time by calculating a difference from a first elapsed time, which includes a time point when the irradiation detector detects the irradiation to the first time point, to a second elapsed time, which includes the time point when the irradiation detector detects the irradiation to the second time point.

7. The device of claim 5, further comprising:
  a target including the element, the target being disposed at the first measurement point; and
  a gamma ray monitor configured to detect a gamma ray emitted from the target.

8. The device of claim 7, further comprising:
  a mobile pedestal configured to be movable on the subject body, the mobile pedestal supporting the neutron ray source and the gamma ray monitor.

* * * * *